(12) United States Patent
Dolazza et al.

(10) Patent No.: US 6,678,350 B2
(45) Date of Patent: Jan. 13, 2004

(54) METHOD OF AND SYSTEM FOR IMPROVING THE SIGNAL TO NOISE CHARACTERISTICS OF IMAGES FROM A DIGITAL X-RAY DETECTOR RECEIVING BI-CHROMATIC X-RAY ENERGY

(75) Inventors: Enrico Dolazza, Boston, MA (US); James G. Coffin, Hudson, MA (US)

(73) Assignee: Analogic Corporation, Peabody, MA (US)

( * ) Notice: Subject to any disclaimer, the term of this patent is extended or adjusted under 35 U.S.C. 154(b) by 6 days.

(21) Appl. No.: 09/962,822

(22) Filed: Sep. 25, 2001

(65) Prior Publication Data

US 2002/0094062 A1 Jul. 18, 2002

Related U.S. Application Data

(60) Provisional application No. 60/236,944, filed on Sep. 29, 2000.

(51) Int. Cl.⁷ .............................................. H05G 1/64
(52) U.S. Cl. ..................................... 378/98.9; 378/98.8
(58) Field of Search ............................. 378/98.8, 98.9, 378/98.11, 98.12, 19, 92

(56) References Cited

U.S. PATENT DOCUMENTS 4,789,930 A * 12/1988 Sones et al. ........... 364/413.13
4,868,857 A * 9/1989 Dobbins, III ................ 378/99
5,933,540 A    8/1999 Lakshminarayanan et al.
6,052,433 A    4/2000 Chao
6,408,050 B1 * 6/2002 Han et al. .................. 378/98.9

OTHER PUBLICATIONS

PCT International Search Report dated Dec. 26, 2001; 3 pages.

* cited by examiner

*Primary Examiner*—David V. Bruce
*Assistant Examiner*—Irakli Kiknadze
(74) *Attorney, Agent, or Firm*—McDermott, Will & Emery

(57) ABSTRACT

A method of improving the signal to noise ratio associated with the output of a digital x-ray detector receiving bi-chromatic x-ray energy includes acquiring a first image from the detector corresponding to x-ray energy at a first energy level, and scaling the first image with a first scaling factor so as to produce a scaled first image. The method further includes acquiring a second image from the detector corresponding to x-ray energy at a second energy level, and scaling the second image with a second scaling factor so as to produce a second scaled image. The method also includes combining the first scaled image and the second scaled image so as to form a compensated image.

15 Claims, 2 Drawing Sheets

METHOD OF AND SYSTEM FOR IMPROVING THE SIGNAL TO NOISE CHARACTERISTICS OF IMAGES FROM A DIGITAL X-RAY DETECTOR RECEIVING BI-CHROMATIC X-RAY ENERGY

CROSS-REFERENCE TO RELATED APPLICATIONS

This application is related to the following U.S. patent application, of common assignee, from which priority is claimed, and the content of which is incorporated herein in its entirety by reference:

"Method of Improving the Signal to Noise Ratio for a Digital X-Ray Detector Receiving Bi-Chromatic X-Ray Energy," U.S. Provisional Patent Application Serial No. 60/236,944 filed Sep. 29, 2000.

STATEMENT REGARDING FEDERALLY SPONSORED RESEARCH

Not Applicable

REFERENCE TO MICROFICHE APPENDIX

Not Applicable

BACKGROUND OF THE INVENTION

The present invention relates to digital radiography, and more particularly, to digital radiography signal processing techniques for improving signal to noise ratios of an image generated from a bi-chromatic x-ray beam.

X-ray images of non-homogeneous material simultaneously display areas of different attenuation. In some cases, the attenuation differences are significant. For example, chest images simultaneously display areas of great attenuation (e.g., mediastine, spine) and areas of little attenuation (e.g., lungs). Optimum x-ray imaging of these two differing anatomical structures requires different parameters of x-ray flux. Specifically, areas of higher attenuation are better visualized by utilizing lower energy photons, whereas areas of lower attenuation are better visualized by utilizing higher energy photons. For this reason, chest images are generally taken with x-ray photons having a broad energy spectrum or, as it is done in certain procedures recently developed, heat images are taken with two narrow band x-ray pulses that have different average energies.

In both cases, the signal to noise ratio of the images so obtained is lower than the signal to noise ratio of an image obtained with a single narrow band x-ray pulse of the same dosage. The reason for the decreased signal to noise ratio is related to the fact that x-ray photons of different energies generate a different average amount of charge. As a result, the variance of the measured charge signal is affected by both the statistical variance of the photons, and the variance of the charge generated of them. This is known as "Schwank effect."

The following description quantifies the decrease of the signal to noise ratio of an image taken with a bichromatic (i.e., two energy) x-ray beam, with respect to the signal to noise of an image taken with a monochromatic beam, assuming that the two beams have the same number of x-ray photons.

Monochromatic X-ray Beam: Single Image

In the case of a single image I produced from a monochromatic (i.e., one energy level) x-ray beam, the signal S and noise σ of the image I is given by:

$$S = \alpha N \sigma = \alpha \sqrt{N}$$
$$(S/\sigma)^2 = N$$

where N is the average number of x-ray photons detected (i.e., the average photon flux per unit area), and α is the average number of electrons generated per photon. The parameter α is characterized by a single value at least in first approximation, because the energy of the monochromatic x-ray photons has a narrowband spectrum.

Bichromatic Beam: Single Image

The average number of detected x-ray photons N may be partitioned into two groups as follows: $N_1$ photons generate $\alpha_1$ carriers/photon and $N_2$ photons generate $\alpha_2$ carriers/photon, such that $N_1 + N_2 = N$. The $N_1$ photons are relatively narrowband with a single mean energy $E_1$, and the $N_2$ photons are relatively narrowband with a single mean energy $E_2$, with $E_1$ not equal to $E_2$. The signal S and noise σ of the image I is given by:

$$S = \alpha_1 N_1 + \alpha_2 N_2 \quad \sigma = \sqrt{\alpha_1^2 N_1 + \alpha_2^2 N_2}$$

$$(S/\sigma)^2 = \frac{(\alpha_1 N_1 + \alpha_2 N_2)^2}{\alpha_1^2 N_1 + \alpha_2^2 N_2} = \frac{(N_1 + xN_2)^2}{N_1 + x^2 N_2}$$

id., and $x = \alpha_2 / \alpha_1$

The signal to noise ratio $(S/\sigma)^2$ is a function of x, i.e., $(S/\sigma)^2 = f(x)$.

For $x=1$, i.e., $\alpha_1 = \alpha_2$, the case 2) reduces to the case 1) in which the x-ray beam has monochromatic energy.

It can also be shown that $f(x=1)$ is a maximum of the function f(x), because $$\frac{df(x)}{dx} = 0 \text{ for } x = 1, \text{ and } \frac{d^2 f(x)}{dx^2} < 0 \text{ for } x = 1$$

This means that the signal to noise ratio of the monochromatic case is higher than that of a bichromatic case, when the number of photons is equal in both cases.

It can also be shown that in general, the value $(S/\sigma)^2$ for the monochromatic case is greater than the value $(S/\sigma)^2$ for multi-chromatic beams, including the case of a broadband x-ray beam comprising x-ray photons having a broad energy spectrum. This result is known to those in the art as the "Shwank Effect."

It is an object of the present invention to substantially overcome the above-identified disadvantages and drawbacks of the prior art.

SUMMARY OF THE INVENTION

The foregoing and other objects are achieved by the invention which in one aspect comprises a method of improving the signal to noise ratio associated with the output of a digital x-ray detector receiving bi-chromatic x-ray energy. The method includes acquiring a first image from the detector corresponding to x-ray energy at a first energy level, and scaling the first image with a first scaling factor so as to produce a scaled first image. The method further includes acquiring a second image from the detector corresponding to x-ray energy at a second energy level, and scaling the second image with a second scaling factor so as to produce a second scaled image. The method also includes combining the first scaled image and the second scaled image so as to form a compensated image.

In another embodiment of the invention, the first scaling factor is substantially equal to the product of a ratio and a fixed constant. The ratio is $\alpha_2/\alpha_1$, where $\alpha_2$ is the average number of carriers per photon generated by the x-ray energy at the second energy level, and $\alpha_1$ is the average number of carriers per photon generated by the x-ray energy at the first energy level. The second scaling factor is substantially equal to the fixed constant.

In another embodiment of the invention, combining the first and second scaled images further includes adding the first scaled image to the second scaled image.

In another aspect, the invention comprises a system for improving the signal to noise ratio associated with the output of a digital x-ray detector receiving bi-chromatic x-ray energy. The system includes a first multiplier for multiplying a first scaling factor by a first image acquired from the detector so as to produce a scaled first image. The first image corresponds to x-ray energy at a first energy level. The system also includes a second multiplier for multiplying a second scaling factor by a second image acquired from the detector so as to produce a scaled second image. The second image corresponds to x-ray energy at a second energy level. The system further includes a combiner for combining the first scaled image with the second scaled image so as to produce a composite image.

In another embodiment of the invention, the first scaling factor is substantially equal to the product of a ratio and a fixed constant. The ratio includes the average number of carriers per photon generated by the x-ray energy at the second energy level, divided by the average number of carriers per photon generated by the x-ray energy at the first energy level. The second scaling factor is substantially equal to the fixed constant.

In another embodiment of the invention, the combiner includes an adder, such that the combiner adds the first scaled image to the second scaled image to produce the composite image.

In another aspect, the invention comprises a system for improving the signal to noise ratio associated with an output of a digital x-ray detector that receives bi-chromatic x-ray energy and produces an electrical signal representative of the x-ray energy. The system includes an x-ray source for generating x-ray energy at a first and second energy level, and directing the x-ray energy through an object and toward the detector, so as to project a two-dimensional image of the object onto a surface of the detector. The system further includes an image processor for controlling the x-ray source to cyclically produce x-ray energy alternating between the first energy level and the second energy level. The image processor also formats the electrical signal from the detector to produce, for each energy level, a block of image data representative of the two-dimensional image of the object. The image processor thus alternately produces blocks of image data representative of the first energy level and the second energy level. The system also includes an image compensator for applying scaling factors to the blocks of image data from the image processor for each energy level, so as to produce scaled blocks of image data, and for combining the scaled blocks of image data to produce a compensated image.

In another embodiment of the invention, the image compensator combines pairs of blocks of image data, each pair of blocks including a first block representative of the first energy level, and a second block representative of the second energy level.

In another embodiment of the invention the image compensator combines the blocks of image data by adding the blocks of image data.

In another embodiment of the invention, the image compensator multiplies a first block of image data representative of a first energy level by a first scaling factor, and multiplies a second block of image data representative of a second energy level by a second scaling factor.

In another embodiment of the invention, the first scaling factor is $k(\alpha_2/\alpha_1)$ and the second scaling factor is k. $\alpha_1$ is the average number of carriers per photon generated by the x-ray energy at the first energy level, $\alpha_2$ is the average number of carriers per photon generated by the x-ray energy at the second energy level, and k is a fixed constant.

In another aspect, the invention comprises a method of improving a signal to noise ratio associated with an output of a digital x-ray detector receiving bi-chromatic x-ray energy and producing an electrical signal representative of the x-ray energy. The method includes generating x-ray energy at a first energy level and at a second level, and directing the x-ray energy through an object and toward the detector, so as to project a two-dimensional image of the object onto a surface of the detector. The method further includes controlling the x-ray source to cyclically produce x-ray energy alternating between the first energy level and the second energy level. The method also includes formatting the electrical signal from the detector to produce, for each energy level, a block of image data representative of the two-dimensional image of the object. The image processor thus alternately produces blocks of image data representative of the first energy level and the second energy level. The method further includes applying scaling factors to the blocks of image data from the image processor for each energy level, so as to produce scaled blocks of image data, and combining the scaled blocks of image data to produce a compensated image.

Another embodiment of the invention further includes combining pairs of blocks of image data, each pair of blocks including a first block representative of the first energy level, and a second block representative of the second energy level.

Another embodiment of the further includes combining the blocks of image data by adding the blocks of image data.

Another embodiment of the invention further includes multiplying a first block of image data representative of a first energy level by a first scaling factor, and multiplying a second block of image data representative of a second energy level by a second scaling factor.

In another embodiment of the invention, the first scaling factor is $k(\alpha_2/\alpha_1)$ and the second scaling factor is k. $\alpha_1$ is the average number of carriers per photon generated by the x-ray energy at the first energy level, $\alpha_2$ is the average number of carriers per photon generated by the x-ray energy at the second energy level, and k is a fixed constant.

In another aspect, the invention comprises a method of improving a signal to noise ratio associated with an output of a digital x-ray detector receiving multi-chromatic x-ray energy. The method includes acquiring two or more x-ray images from the detector, each acquired image corresponding to x-ray energy received at one of two or more energy levels. The method further includes scaling each of the two or more images with an associated scaling factor so as to produce a set of scaled images. The method also includes combining the set of scaled images so as to form a compensated image.

In another embodiment of the invention, combining the set of scaled images includes adding the set of scaled images together.

In another aspect, the invention comprises a system for improving a signal to noise ratio associated with an output of a digital x-ray detector that receives multi-chromatic x-ray energy and produces an electrical signal representative of the x-ray energy. The system includes an x-ray source for generating x-ray energy at two or more energy levels, and directing the x-ray energy through an object and toward the detector, so as to project a two-dimensional image of the object onto a surface of the detector. The system also includes an image processor for controlling the x-ray source to cyclically produce x-ray energy alternating among the two or more energy levels. The image processor also formats the electrical signal from the detector to produce, for each of the two or more energy levels, a block of image data representative of the two-dimensional image of the object. The image processor thus cyclically produces blocks of image data representative of the two or more energy levels. The system further includes an image compensator for applying scaling factors to the blocks of image data from the image processor for each energy level, so as to produce scaled blocks of image data, and for combining the scaled blocks of image data to produce a compensated image.

Another embodiment of the invention, the image compensator combines sets of N blocks of image data, wherein N represents a total number of energy levels produced by the x-ray source.

Another embodiment of the invention, the image compensator combines the blocks of image data by adding the blocks of image data.

BRIEF DESCRIPTION OF DRAWINGS

The foregoing and other objects of this invention, the various features thereof, as well as the invention itself, may be more fully understood from the following description, when read together with the accompanying drawings in which.

DESCRIPTION OF THE PREFERRED EMBODIMENTS

Figure 1:
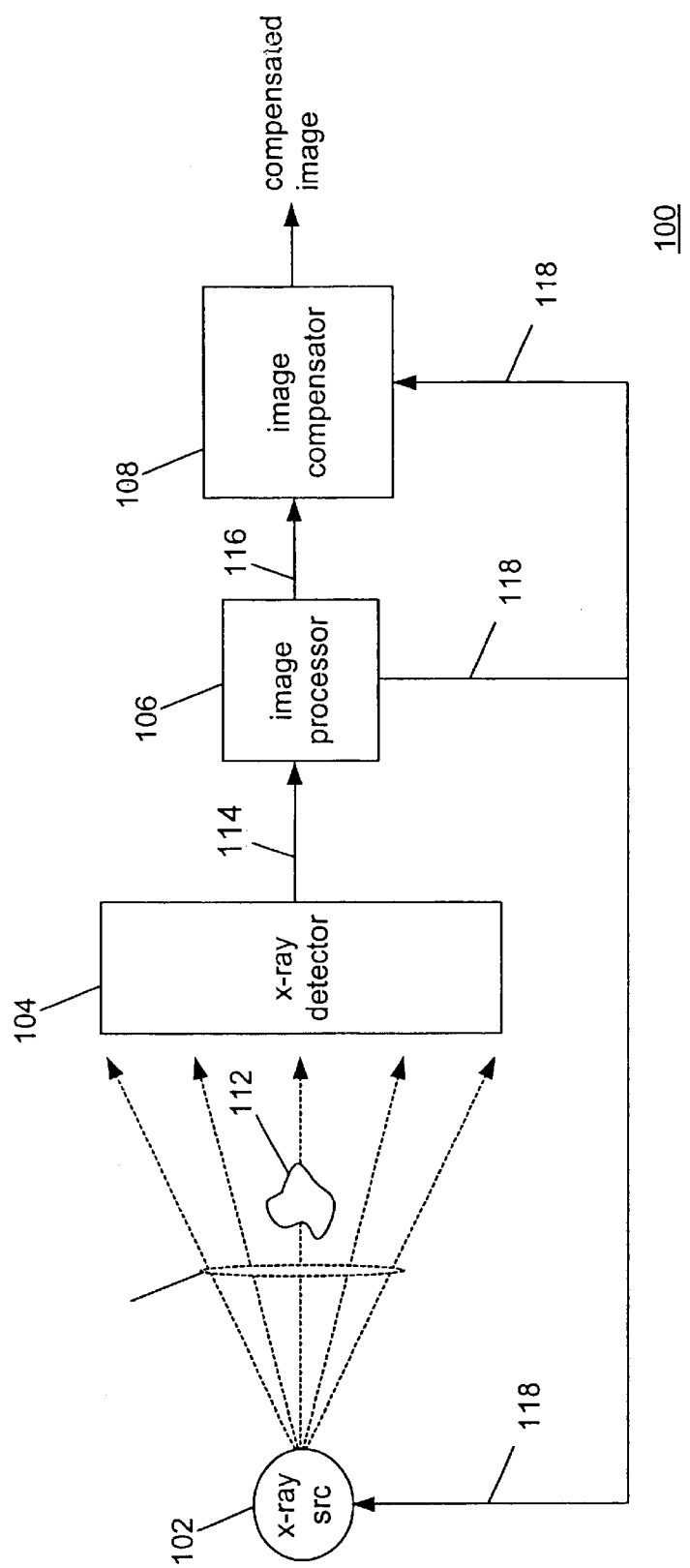
FIG. 1 shows one preferred embodiment of a system for improving the signal to noise characteristics associated with the image derived from an digital x-ray detector that receives bi-chromatic x-ray energy, according to the present invention.

FIG. 1 illustrates one preferred embodiment of a system 100 for improving the signal to noise characteristics associated with the image derived from an digital x-ray detector that receives bi-chromatic x-ray energy. The system 100 includes an x-ray source 102, an x-ray detector 104, an image processor 106 and an image compensator 108. The x-ray source 102 directs x-ray energy 110 through an object 112 and onto the detector 104. The x-ray beam 110 is typically restricted to only the object 112 via techniques known to those in the art (i.e., collimators, screens, shields, etc.). The components implementing these restricting techniques are not depicted in FIG. 1. The object 112 selectively attenuates the x-ray beam 110 as it passes through the object 112; thus, the x-ray beam projects a two-dimensional image of the object 112 upon the surface of the detector 104. The x-ray detector 104 produces an electrical signal 114 corresponding to the x-ray energy that reaches the detector 104. Therefore, the electrical signal 114 includes information that is representative of a projected, two-dimensional image of object 112. The image processor 106 receives the electrical signal 114, formats the image information from the signal 114 and produces one or more blocks of image data 116, each block corresponding to the projection of the object 112 onto the detector 104. The image compensator 108 receives the one or more blocks of information 116 from the image processor 106 and produces a compensated image that is a function of the blocks of image data as described herein.

In one preferred embodiment, the x-ray source 102 is capable of producing x-ray energy at a first energy level and x-ray energy at a second energy level. Although the source 102 may be capable of producing x-ray energy at both energy levels simultaneously, the x-ray source 102 preferably produces either x-ray energy at first energy level or x-ray energy at a second energy level, but not both. The x-ray source 102 produces x-ray energy at one of the two energy levels in response to a control signal 118 from the image processor 106. In one preferred embodiment, the image processor 106 controls the system 100 such that the x-ray source 102, the detector 104 and the image processor 106 cyclically operate between a first state and a second state (i.e., first state, second state, first state, second state, etc.). In the first state, the image processor sets the x-ray source to produce x-ray energy at a first energy level via the control signal 118. The image processor 106 acquires a block of image data from the detector 104 corresponding to the first energy level. The image processor 106 then sets the x-ray source to produce energy at the second energy level via the control signal 118. The image processor 106 then acquires a block of image data from the detector 104 corresponding to the second energy level.

The image compensator 108 thus receives cyclically alternating blocks of image data from the image processor representing x-ray energy at high and low energy levels. The image compensator 108 operates on pairs of image data blocks. Each compensated image from the compensator 108 comprises a weighted (also referred to herein as "scaled") combination of a first block of image data (at the first energy level) and a second block of image data (at the second energy level). One embodiment of the image compensator 108, shown in more detail in FIG. 2, includes a multiplexor 120, a first multiplier 122, a second multiplier 124 and a combiner 126. In one preferred embodiment, the combiner 126 includes a summer for adding the scaled inputs from the multipliers 122 and 124, although other methods of combining known in the art may also be used. For example, the combiner 126 could multiply the two inputs. Also, the combiner 126 could perform a "sum of the squares" operation by squaring each of the inputs and adding the squared inputs, then taking the square root of the result. Similarly, the combiner 126 could raise the inputs to different powers prior to summing.

The multiplexor 120 receives the cyclically alternating blocks of image data from the image processor 106 and alternately routes a first block of image data (at the first energy level) to the first multiplier 122, and a second block of image data (at the second energy level) to the second multipler 124.

The signal $S_1$ and the noise $\sigma_1$ of the first block of image data $I_1$ are given by:

$$S_1 = \alpha_1 N_1 \quad \sigma_1 = \alpha_1 \sqrt{N_1},$$

where $N_1$ photons generate $\alpha_1$ carriers/photon, and the signal $S_2$ and the noise $\sigma_2$ of the second block of image data $I_2$ are given by:

$$S_2 = \alpha_2 N_2 \quad \sigma_2 = \alpha_2 \sqrt{N_2}$$

where $N_2$ photons generate $\alpha_2$ carriers/photon. Preferably, $I_1$ and $I_2$ are independent image acquisitions. The compensated image I at the output of the combiner 126 is obtained by summing $I_1$ and $I_2$ after applying different weights (also referred to herein as "scaling factors"), i.e., $$I = I_1 x k + I_2 k$$

where $x = \alpha_2/\alpha_1$ and k is an arbitrary constant.

Figure 2:
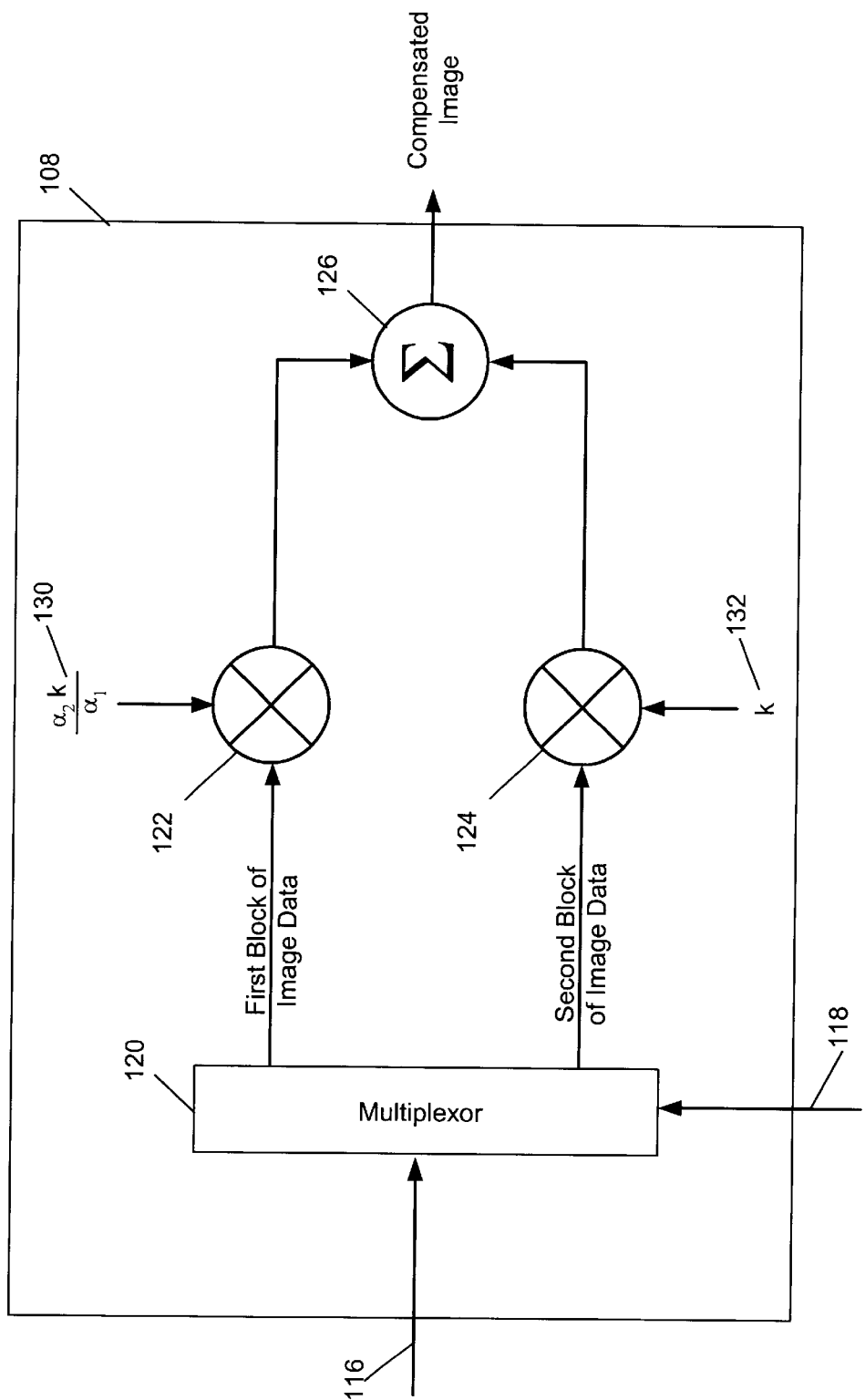
FIG. 2 shows a more detailed view of the image compensator from the system of FIG. 1.

In other words, the "compensation" includes scaling the independent image acquisitions and summing the scaled acquisitions to provide resulting image I. In FIG. 2, the first multiplier 122 receives a first weighting value 130 substantially equal to $k(\alpha_2/\alpha_1)$ and multiplies the first weighting value 130 by the first block of image data $I_1$. The second multiplier 124 receives a second weighting value 132 substantially equal to the constant k, and multiplies the second weighting value 132 by the second block of image data $I_2$.

The signal and the noise of I are given by:

$$S = k\alpha_2(N_1 + N_2) = k\alpha_2 N$$

$$\sigma = \sqrt{\sqrt{k^2 \alpha_2^2 N_1 + k^2 \alpha_2^2 N_2}} = k\alpha_2 \sqrt{N}$$

Notice that for $k = \alpha/\alpha_2$, both S and $\sigma$ of the present invention are identical to those of the monochromatic case described herein, and that the signal to noise ratio is $S/\sigma^2 = N$, independent of the choice of the arbitrary constant k. The compensation of the image acquisitions (i.e., scaling and subsequent summing of the independent acquisitions $I_1$ and $I_2$) thus eliminates the signal/noise reduction due to the "bichromaticity."

Although the embodiment described herein compensates an image generated from x-ray energy at two distinct levels, similar scaling and summing of multiple beams (i.e., greater than two) can be used to similarly reduce or eliminate the signal/noise degradation with respect to the monochromatic case.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A method of improving a signal to noise ratio associated with an output of a digital x-ray detector receiving bi-chromatic x-ray energy, comprising:

acquiring from the detector a first image corresponding to x-ray energy at a first energy level, and scaling the first image with a first scaling factor so as to produce a scaled first image;

acquiring from the detector a second image corresponding to x-ray energy at a second energy level, and scaling the second image with a second scaling factor so as to produce a second scaled image; and, combining the first scaled image and the second scaled image so as to form a compensated image wherein the first scaling factor is substantially equal to the product of i) the ratio of the average number of carriers per photon generated by the x-ray energy at the second energy level to the average number of carriers per photon generated by the x-ray energy at the first energy level, and ii) a fixed constant, and the second scaling factor is substantially equal to the fixed constant.

2. A method according to claim 1, wherein combining the first and second scaled images includes adding the first scaled image to the second scaled image.

3. A system for improving a signal to noise ratio associated with an output of a digital x-ray detector receiving bi-chromatic x-ray energy, comprising:

a first multiplier for multiplying a first scaling factor by a first image acquired from the detector so as to produce a scaled first image, the first image corresponding to x-ray energy at a first energy level;

a second multiplier for multiplying a second scaling factor by a second image acquired from the detector so as to produce a scaled second image, the second image corresponding to x-ray energy at a second energy level; and, a combiner for combining the first scaled image with the second scaled image so as to produce a composite image wherein the first scaling factor is substantially equal to the product of i) the ratio of the average number of carriers per photon generated by the x-ray energy at the second energy level to the average number of carriers per photon generated by the x-ray energy at the first energy level, and ii) a fixed constant, and the second scaling factor is substantially equal to the fixed constant.

4. A system according to claim 3, wherein the combiner includes an adder, such that the combiner adds the first scaled image to the second scaled image to produce the composite image.

5. A method of improving a signal to noise ratio associated with an output of a digital x-ray detector receiving multi-chromatic x-ray energy, comprising:

acquiring from the detector two or more x-ray images, each acquired image corresponding to x-ray energy received at one of two or more energy levels scaling each of the two or more images with an associated scaling factor so as to produce a set of scaled images, wherein each of said scaling factors is a function of the average number of carriers per photon generated by the associated x-ray energy; and, combining the set of scaled images so as to form a compensated image.

6. A method according to claim 5, wherein combining the set of scaled images includes adding the set of scaled images together.

7. A system for improving a signal to noise ratio associated with an output of a digital x-ray detector that receives multi-chromatic x-ray energy and produces an electrical signal representative of the x-ray energy, comprising:

an x-ray source for generating x-ray energy at two or more energy levels, and directing the x-ray energy through an object and toward the detector, so as to project a two-dimensional image of the object onto a surface of the detector;

an image processor (i) for controlling the x-ray source to cyclically produce x-ray energy alternating among the two or more energy levels, and (ii) for formatting the electrical signal from the detector to produce, for each of the two or more energy levels, a block of image data representative of the two-dimensional image of the object, such that the image processor cyclically produces blocks of image data representative of the two or more energy levels; and, an image compensator for applying a scaling factors to the blocks of image data from the image processor for each corresponding energy level, so as to produce scaled blocks of image data, and for combining the scaled blocks of image data to produce a compensated image wherein the scaling factor applied to each of the blocks of image processor for each corresponding energy level is a function of the average number of carriers per photon generated by the associated x-ray energy.

8. A system according to claim 7, wherein the image compensator combines sets of N blocks of image data, wherein N represents a total number of energy levels produced by the x-ray source.

9. A system according to claim 7, wherein the image compensator combines the blocks of image data by adding the blocks of image data.

10. A system for improving a signal to noise ratio associated with an output of a digital x-ray detector that receives bi-chromatic x-ray energy and produces an electrical signal representative of the x-ray energy, comprising:

an x-ray source for generating x-ray energy at a first energy level and at a second level, and directing the x-ray energy through an object and toward the detector, so as to project a two-dimensional image of the object onto a surface of the detector;

an image processor (i) for controlling the x-ray source to cyclically produce x-ray energy alternating between first energy levels, and (ii) for formatting the electrical signal from the detector to produce, for each energy level, a block of image data representative of the two-dimensional image of the object, such that the image processor alternately produces blocks of image data representative of the first energy levels and the second energy level; and, an image compensator for applying scaling factors to the blocks of image data from the image processor for each energy level, so as to produce scaled blocks of image data, and for combining the scaled blocks of image data to produce a compensated image;

wherein the image compensator multiplies a first block of image data representative of a first energy level by a first scaling factor, and multiplies a second block of image data representative of a second energy level by a second scaling factor; and the first scaling factor is $k(\alpha_2/\alpha_1)$ and the second scaling factor is k, $\alpha_1$ being the average number of carriers per photon generated by the x-ray energy at the first energy level, $\alpha_2$ being the average number of carriers per photon generated by the x-ray energy at the second energy level, and k being a fixed constant.

11. A system according to claim 10, wherein the image compensator combines pairs of blocks of image data, each pair of blocks including a first block representative of the first energy level, and a second block representative of the second energy level.

12. A system according to claim 10, wherein the image compensator combines the blocks of image data by adding the blocks of image data.

13. A method of improving a signal to noise ratio associated with an output of a digital x-ray detector receiving bi-chromatic x-ray energy and producing an electrical signal representative of the x-ray energy, comprising:

generating x-ray energy at a first energy level and a second level, and directing the x-ray energy through an object and toward the detector so as to project a two-dimensional image of the object onto a surface of the detector;

controlling the x-ray source to cyclically produce x-ray energy alternating between the first energy level and the second energy level;

formatting the electrical signal from the detector to produce, for each energy level, a block of image data representative of the two-dimensional image of the object, such that the image processor alternately produces blocks of image data representative of the first energy level and the second energy level; and, applying scaling factors to the blocks of image data from the image processor for each energy level, so as to produce scaled blocks of image data, and combining the scaled blocks of image data to produce a compensated image, wherein applying scaling factors includes multiplying a first block of image data representative of a first energy level by a first scaling factor, and multiplying a second block of image data representative of a second energy level by a second scaling factor wherein the first scaling factor is $k(\alpha_2/\alpha_1)$ and the second scaling factor is k, $\alpha_1$ being the average number of carriers per photon generated by the x-ray energy at the first energy level, $\alpha_2$ being the average number of carriers per photon generated by the x-ray energy at the second energy level, and k being a fixed constant.

14. A method according to claim 13, further including combining pairs of blocks of image data, each pair of blocks including a first block representative of the first energy level, and a second block representative of the second energy level.

15. A method according to claim 13, further including combining the blocks of image data by adding the blocks of image data.

* * * * *

UNITED STATES PATENT AND TRADEMARK OFFICE
CERTIFICATE OF CORRECTION

PATENT NO.     : 6,678,350 B2
DATED          : January 13, 2004
INVENTOR(S)    : Enrico Dolazaa et al.

It is certified that error appears in the above-identified patent and that said Letters Patent is hereby corrected as shown below:

Column 9,
Line 23, from the beginning, delete "first energy levels", and insert thereof -- the first energy level and the second energy level --;

Signed and Sealed this

Twentieth Day of April, 2004

JON W. DUDAS
*Acting Director of the United States Patent and Trademark Office*